(12) United States Patent
Lopez et al.

(10) Patent No.: US 9,696,243 B2
(45) Date of Patent: Jul. 4, 2017

(54) FLUID SAMPLING SYSTEM

(75) Inventors: Jose Lopez, Sherbrooke (CA); Michel Lepitre, Orford (CA)

(73) Assignees: Jose Lopez, Sherbrooke (CA); Michel Lepitre, Orford (CA); Fiducie Aeternum, Sherbrooke (CA)

( * ) Notice: Subject to any disclaimer, the term of this patent is extended or adjusted under 35 U.S.C. 154(b) by 944 days.

(21) Appl. No.: 13/521,760

(22) PCT Filed: Jan. 11, 2011

(86) PCT No.: PCT/CA2011/000029
§ 371 (c)(1),
(2), (4) Date: Aug. 30, 2012

(87) PCT Pub. No.: WO2011/085475
PCT Pub. Date: Jul. 21, 2011

(65) Prior Publication Data
US 2013/0000392 A1   Jan. 3, 2013

Related U.S. Application Data

(60) Provisional application No. 61/294,134, filed on Jan. 12, 2010.

(51) Int. Cl.
*G01N 1/20* (2006.01)

(52) U.S. Cl.
CPC ... *G01N 1/2035* (2013.01); *G01N 2001/2071* (2013.01)

(58) Field of Classification Search
CPC .............. G01N 2001/2035; G01N 2001/2071
See application file for complete search history.

(56) References Cited

U.S. PATENT DOCUMENTS

| | | | | |
|---|---|---|---|---|
| 1,837,858 A | * | 12/1931 | Grace | G01N 1/14 159/30 |
| 3,013,431 A | * | 12/1961 | Splettstoeser | A01J 5/01 119/14.17 |
| 3,083,577 A | * | 4/1963 | Moore | G01N 1/2035 137/599.01 |
| 3,429,186 A | * | 2/1969 | Price | G01N 1/22 73/863.61 |
| 3,930,414 A | * | 1/1976 | Russell | G01N 1/2035 73/863.03 |
| 3,950,136 A | * | 4/1976 | Bellinga | G01N 1/22 422/83 |
| 4,174,632 A | * | 11/1979 | Jansen | G01N 1/2035 73/863.86 |
| 4,651,574 A | * | 3/1987 | Spencer | G01N 1/2035 141/301 |
| 4,928,541 A | * | 5/1990 | Toon | G01N 1/12 73/864.63 |
| 4,947,468 A | * | 8/1990 | Nelson | G01R 29/24 324/453 |

(Continued)

*Primary Examiner* — John Fitzgerald
(74) *Attorney, Agent, or Firm* — Norton Rose Fulbright Canada LLP

(57) ABSTRACT

A fluid sampling system for collecting a fluid sample, the sampling system comprising a detachable sampling device having a recipient, an entrance valve for controlling entry of a fluid into the recipient, an exit valve for controlling exit of the fluid from the recipient, and a data storage device for storing data related to the fluid sample.

9 Claims, 14 Drawing Sheets

(56) References Cited

U.S. PATENT DOCUMENTS

| | | | | |
|---|---|---|---|---|
| 5,005,432 | A * | 4/1991 | Faulkner | G01N 1/2035 73/863.86 |
| 5,103,212 | A * | 4/1992 | Notarianni | G08B 17/10 340/628 |
| 5,353,651 | A * | 10/1994 | Pate | F16L 37/23 73/861.85 |
| 5,674,381 | A * | 10/1997 | Den Dekker | 210/85 |
| 5,880,380 | A * | 3/1999 | Goldschmidt | G01N 1/2035 73/863.84 |
| 6,186,140 | B1 * | 2/2001 | Hoague | 128/202.22 |
| 6,558,444 | B1 * | 5/2003 | Hunter | 55/385.1 |
| 6,636,812 | B2 * | 10/2003 | Pegram | G01N 1/2035 356/417 |
| 6,904,370 | B1 * | 6/2005 | Levinson et al. | 702/19 |
| 6,947,866 | B2 * | 9/2005 | Staab | 702/150 |
| 7,008,793 | B2 * | 3/2006 | Duriez | E21B 49/08 436/28 |
| 7,121,156 | B2 * | 10/2006 | Anschutz | G01N 1/2202 73/863.61 |
| 7,302,313 | B2 * | 11/2007 | Sharp et al. | 700/276 |
| 7,360,400 | B2 * | 4/2008 | Baumfalk et al. | 73/38 |
| 7,638,042 | B2 * | 12/2009 | Astle et al. | 210/85 |
| 7,736,495 | B2 * | 6/2010 | Ikeyama et al. | 210/85 |
| 7,790,022 | B2 * | 9/2010 | Underwood et al. | 210/91 |
| 7,938,029 | B2 * | 5/2011 | Campbell | G01N 1/2035 73/863.83 |
| 8,221,522 | B2 * | 7/2012 | DiLeo et al. | 95/19 |
| 8,303,698 | B2 * | 11/2012 | Grzonka et al. | 96/417 |
| 8,322,233 | B2 * | 12/2012 | Hennen et al. | 73/864.91 |
| 2002/0041832 | A1 * | 4/2002 | Duriez | E21B 49/08 436/29 |
| 2003/0168389 | A1 * | 9/2003 | Astle et al. | 210/85 |
| 2005/0223996 | A1 * | 10/2005 | Bosma | A01J 5/01 119/14.02 |
| 2006/0060512 | A1 * | 3/2006 | Astle et al. | 210/85 |
| 2006/0102844 | A1 * | 5/2006 | Sauer | G01N 21/3504 250/339.13 |
| 2006/0157391 | A1 * | 7/2006 | Astle et al. | 210/85 |
| 2006/0169066 | A1 * | 8/2006 | Anschutz | G01N 1/2202 73/863.83 |
| 2008/0034900 | A1 * | 2/2008 | Bollinger | G01N 1/14 73/864.73 |
| 2008/0047370 | A1 * | 2/2008 | Vickery | G01N 1/2214 73/863.21 |
| 2008/0098827 | A1 * | 5/2008 | Campbell | G01N 1/2035 73/863 |
| 2008/0281528 | A1 * | 11/2008 | Relle, Jr. | 702/19 |
| 2009/0225808 | A1 * | 9/2009 | DiLeo | 374/141 |
| 2010/0096302 | A1 * | 4/2010 | Astle et al. | 210/85 |
| 2010/0104473 | A1 * | 4/2010 | Kirollos | G01N 1/2273 422/400 |
| 2011/0205073 | A1 * | 8/2011 | Calio | G01N 1/26 340/606 |

\* cited by examiner

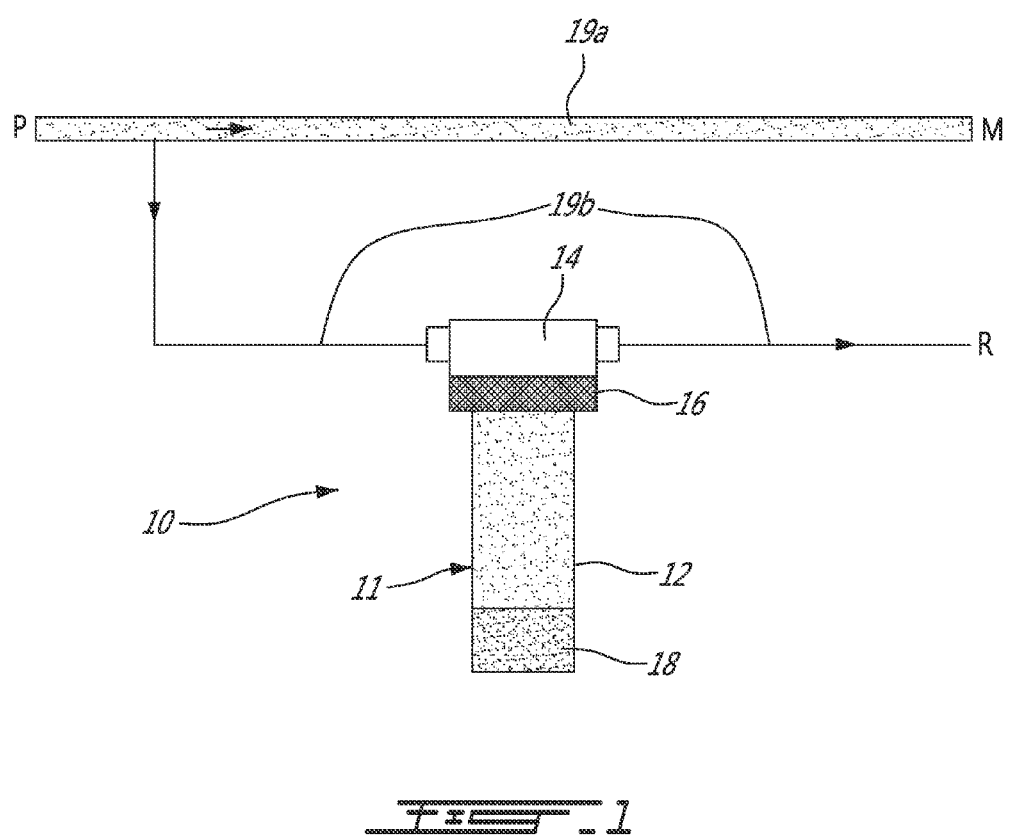

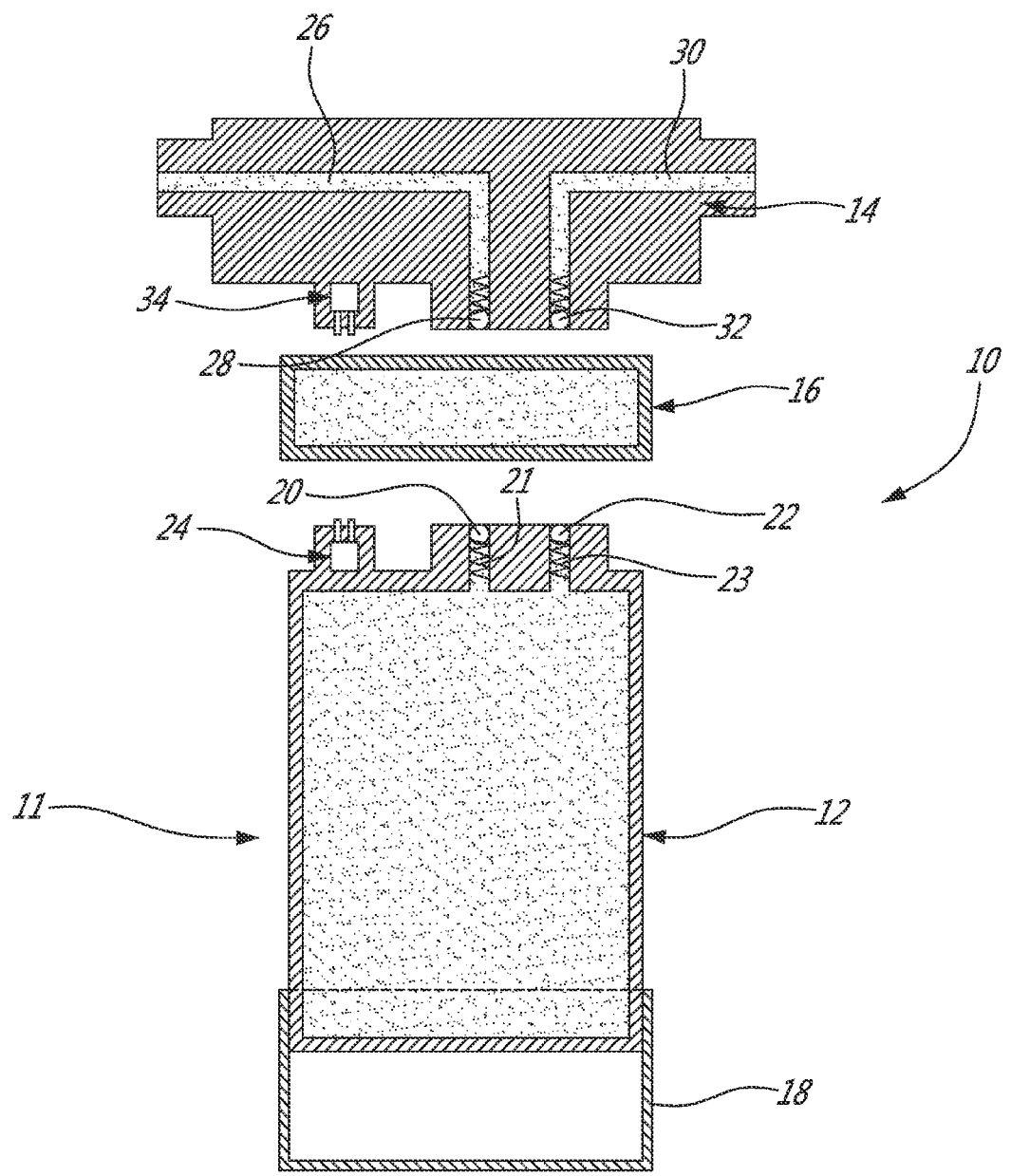

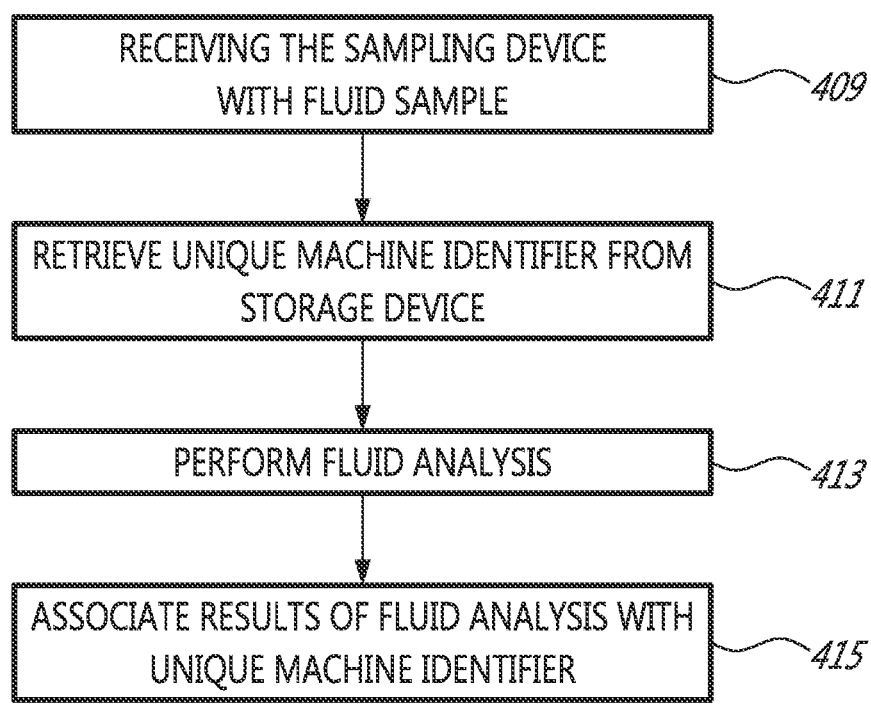

FLUID SAMPLING SYSTEM

CROSS-REFERENCE TO RELATED APPLICATIONS

This application claims priority under 35 U.S.C. §119(e) from U.S. Provisional Patent Application No. 61/294,134, filed on Jan. 12, 2010, the contents of which are hereby incorporated by reference.

TECHNICAL FIELD

The present invention relates to the field of fluid sampling and more particularly, to collecting fluid samples from machines, such as vehicles (planes, trains, boats, trucks, cars) or industrial-type machinery.

BACKGROUND OF THE ART

Fluid sampling is performed in a number of fields for testing purposes in order to learn more information about a particular fluid, such as its composition, properties, etc. Fluid sampling typically requires a manual sampling operation which is performed by a person, in order to collect a specimen in, for example, a vial. The specimen is then sent to a laboratory for testing of the particular fluid.

During the manual collection of fluid samples, errors may arise such that the fluid sample becomes contaminated and its composition differs from the original fluid from which the fluid sample is taken. Due to the complexity of manual sampling operations and the risk of fluid sample contamination, manual sampling of a fluid may require a large amount of time and so limit the amount of samples which may be taken on any given day by a finite number of people. Furthermore, when fluid samples are sent to a laboratory for testing, misidentification problems may arise such that fluid samples are misplaced or incorrectly identified as coming from a different source or as sampled at a different date or time.

Therefore, there exists room for improvement in the art of fluid sampling.

SUMMARY

There is described herein a fluid sampling system that allows for collection of a representative sample of fluid flowing in a fluid system such that fluid contamination risks are reduced. There is also described a method of collecting the fluid sample, and a method of tracking the fluid sample, for process standardization.

In accordance with a first broad aspect, there is provided a fluid sampling system for collecting a fluid sample from a fluid system of a machine, the sampling system comprising: at least one base having at least one base conduit for receiving fluid from the fluid system and flowing it through the base; and a sampling device detachably connectable to the base for fluid flow communication therewith, the sampling device having a recipient, a recipient entrance conduit for mating with the at least one base conduit so as to admit fluid from the base into the recipient, and a recipient exit conduit for allowing fluid to exit the recipient and flow back into the fluid system.

In accordance with a second broad aspect, there is provided a fluid sampling system for collecting a fluid sample, the sampling system comprising a detachable sampling device having a recipient, an entrance valve for controlling entry of a fluid into the recipient, an exit valve for controlling exit of the fluid from the recipient, and a data storage device for storing data related to the fluid sample.

In accordance with a third broad aspect, there is provided a method for collecting a fluid sample from a fluid system of a machine using a fluid sampling system, the method comprising: connecting a sampling device of the fluid sampling system to the fluid system of the machine; collecting the fluid sample from the fluid system of the machine inside the sampling device; storing information related to the fluid sample inside a data storage device of the sampling device; and disconnecting the sampling device from the fluid system of the machine and sealing the contents thereof.

In accordance with a fourth broad aspect, there is provided a method for tracking a fluid sample collected from a fluid system of a machine, the method comprising: receiving a sampling device having the fluid sample contained in a recipient thereof, the sampling device comprising a data storage device storing a unique machine identifier corresponding to the machine from which the fluid sample was taken; retrieving the unique machine identifier from the data storage device; performing fluid analysis on the fluid sample; and associating results of the fluid analysis with the unique machine identifier.

BRIEF DESCRIPTION OF THE DRAWINGS

Further features and advantages of the present invention will become apparent from the following detailed description, taken in combination with the appended drawings, in which:

FIG. 1 is a schematic view of a fluid sampling system in accordance with one embodiment, incorporated into a fluid system of a machine;

FIG. 2b is a cross-section view of the fluid sampling system of FIG. 1, with a data storage system incorporated therein, in accordance with one embodiment;

FIG. 13 is a flowchart of a method for tracking a fluid collected from a fluid system, in accordance with one embodiment.

It will be noted that throughout the appended drawings, like features are identified by like reference numerals.

DETAILED DESCRIPTION

Figure 2A:
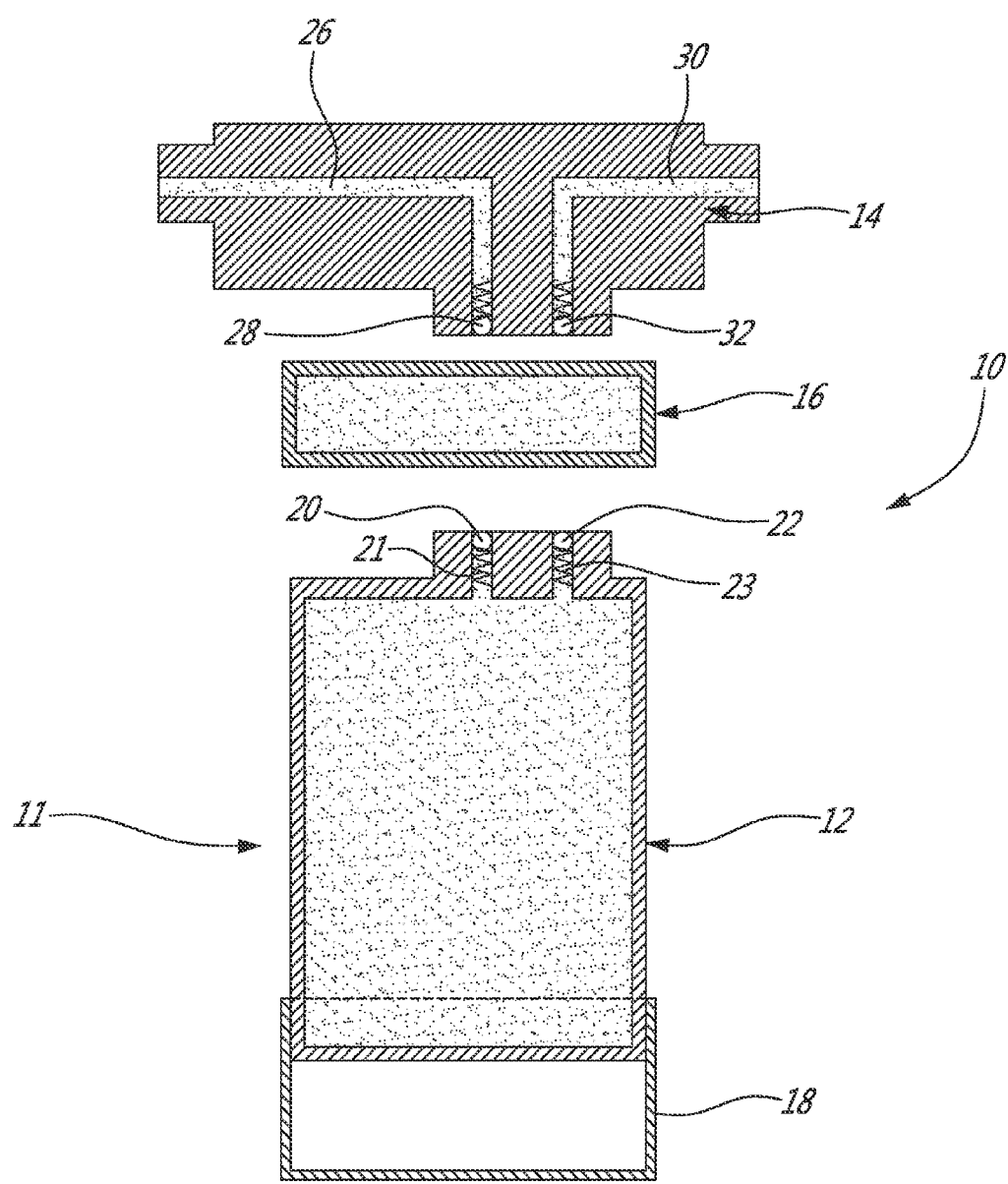
FIG. 2a is a cross-section view of the fluid sampling system of FIG. 1, in accordance with one embodiment.

FIG. 1 shows one embodiment of a fluid sampling system 10 as used with a fluid system of a machine. The fluid sampling system 10 comprises a detachable sampling device 11 which may be connected to a base 14 through the use of a coupler 16 located therebetween. In the particular embodiment of FIG. 1, a pump P may propel fluid through a primary fluid conduit 19a to a machine M. In addition, the pump P may propel fluid through a secondary fluid conduit 19b which passes through the fluid sampling system 10 and on to a reservoir R. It should be noted that the fluid system of the machine shown in FIG. 1 represents but one possible application of the fluid sampling system 10, and in other embodiments, the fluid sampling system 10 may be used with other fluid systems.

As seen in FIG. 2a, the detachable sampling device 11 comprises a recipient 12 and a cap 18 which may be attached to a bottom portion of the recipient when the recipient 12 is in use. The cap 18 may be attached to the recipient 12 using a number of different means, such as fasteners, threads, etc. For example, the recipient 12 may have external threads (not shown) on a bottom portion thereof and the cap 18 may have internal threads (not shown) which mate with the external threads of the recipient, so as to connect the cap 18 and the recipient 12 together. The recipient 12 comprises an entrance valve 20 located inside an entrance conduit 21 for controlling passage of a fluid into the recipient 12, and an exit valve located inside an exit conduit 23 for controlling passage of a fluid out of the recipient 12.

The base 14 may form an integral component of a typical fluid system of a machine or may be a separate component which is attached to the existing fluid system of a machine. The base 14 includes an entrance conduit 26 which may be in fluid flow communication with a fluid conduit 19b of a fluid system of a machine, for allowing fluid to pass into the base 14 of the fluid sampling system 10. An exit valve 28 may be located inside the entrance conduit 26 for controlling passage of the fluid out of the base 14. The base 14 also includes an exit conduit 30 which may be in fluid flow communication with fluid conduit 19b, for allowing fluid to exit from the base 14 of the fluid sampling system 10. An entrance valve 32 may be located inside the exit conduit 30 for controlling passage of the fluid into the base 14 from the recipient 12.

As seen in FIG. 1, the coupler 16 is attached to the base 14 and may be used to interconnect the detachable sampling device 11 to the base 14. When the base 14 is connected to the detachable sampling device 11, the entrance conduit 26 of the base 14 is connected to the entrance conduit 21 of the recipient and the exit conduit 23 of the recipient 12 is connected to the exit conduit 30 of the base 14. The conduits 26, 21, 23 and 30 therefore form a fluid passage into and out of, respectively, the base 14 and the recipient 12, of the fluid sampling system 10. Therefore, when the base 14 is connected to the detachable sampling device 11, fluid may always be circulating through the recipient 12.

The coupler 16 serves to fix the sampling device to the base 14 and to minimize displacement and/or disconnection of the sampling device 11 when it is connected to the base 14. The coupler 16 may also permit activation of the entrance valves 20, 32 and the exit valves 22, 28 of the recipient 12 and the base 14, respectively. When a fluid sample is to be collected, the coupler 16 may be operated such that the sampling device 11 disconnects from the base 14. When the coupler 16 is operated and the sampling device is disconnected, the coupler closes the entrance valves 20, 32 and the exit valves 22, 28, such that fluid may no longer pass through the entrance conduits 21, 26, and the exit conduits 23, 30 of the recipient 12 and the base 14 respectively. This ensures that the fluid sample located inside the recipient 12 is sealed inside the recipient 12 when the coupler is operated to disconnect the sampling device 11, and that any risk of contamination of the fluid sample is minimized.

Figure 3:
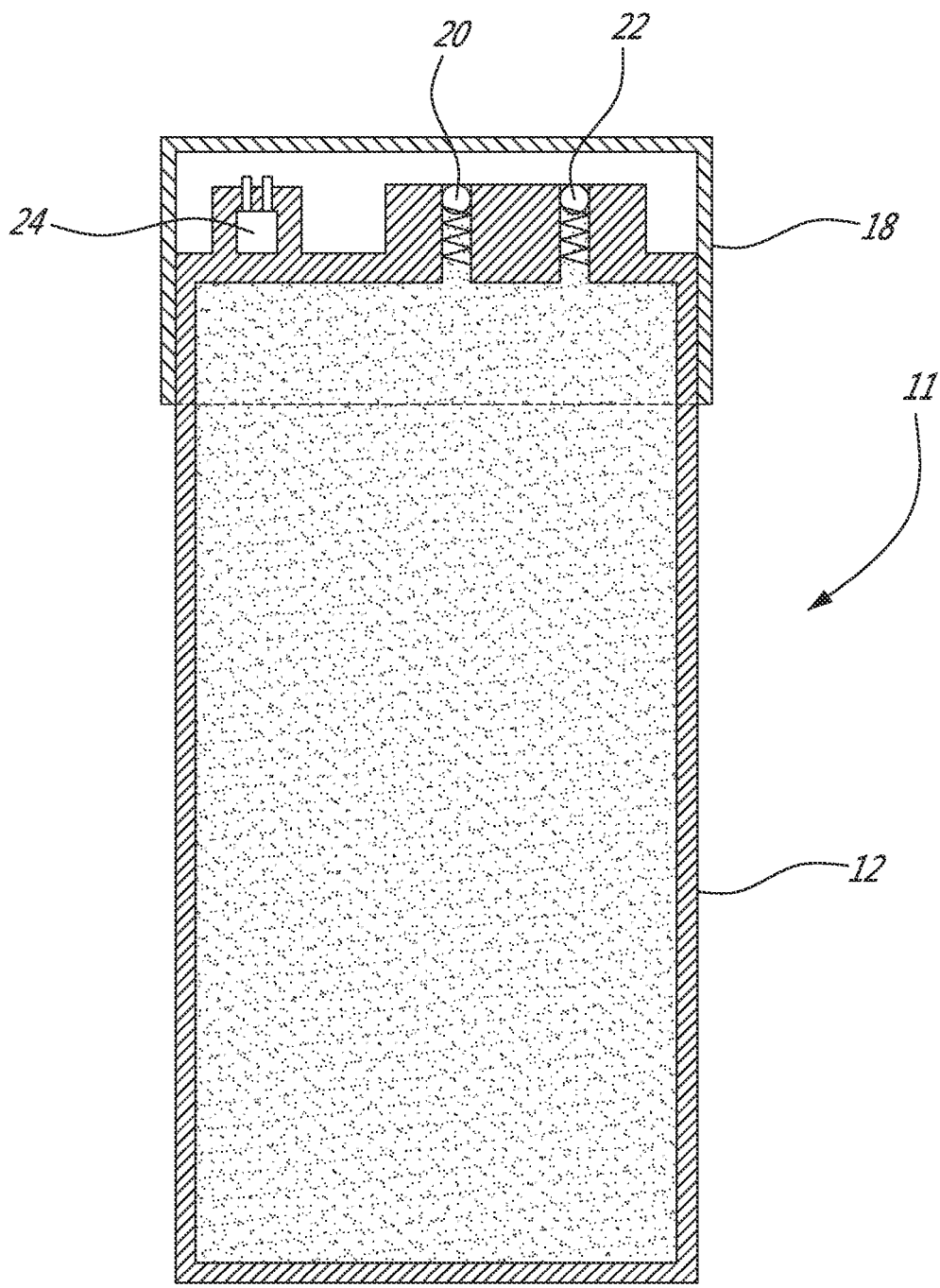
FIG. 3 is a cross-section view of a sampling device of the fluid sampling system of FIG. 1, with a cap on a top thereof, in accordance with one embodiment.

As illustrated in FIG. 3, when the sampling device 11 is released from the base 14, the cap 18 may be removed from the bottom of the recipient 12 and may be attached to the top of the recipient 12, in order to seal and protect the conduits 21, 23 of the recipient 12, during transportation and handling of the sampling device 11. The recipient 12 may include external threads (not shown) on a top thereof, such that the cap 18 may be removed from the bottom of the recipient 12 and may be screwed onto the top of the recipient 12. In another embodiment, the cap 18 may be attached to the top of the recipient 12 using other means, such as fasteners. In one embodiment, the conduits 21, 23 of the recipient may be located in an inner portion of the recipient 12, so as to not protrude therefrom.

When the sampling device 11 has been disconnected from the base 14, the sampling device 11 may be sent to a laboratory for testing and a new sampling device may be connected to the base 14 through the use of the coupler 16. This method of proceeding lowers the risk of contaminating the fluid sample, because little manual operation of the fluid sampling system 10 is required. The fluid sampling system 10 may be used by operating the coupler 16 so as to disconnect the sampling device 11 from the base 14 and by replacing the sampling device 11 by a new sampling device, which is connected to the base 14 by operating the coupler 16 and placing the new sampling device thereon. Afterwards, the cap 18 may be removed from the bottom of the recipient 12 and placed on the top of the recipient 12 for subsequent transportation of the sampling device 11.

The coupler 16 may comprise different types of coupling components. In one embodiment, the coupler 16 comprises a quick connect type fastener, such as a pull-tab fitting, a pinch type fitting, a button type fitting, a latch type fitting, etc. In another embodiment, the coupler 16 comprises a nut type fastener, which may be screwed onto both the base 14 and the sampling device 11. In another embodiment, the coupler may comprise a ring or a sleeve, such as to form a connection between the base 14 and the sampling device 11. In one embodiment, it may not be necessary to operate the coupler 16 in order to connect the sampling device 11 to the base 14, for example the sampling device 11 may be attached to the coupler 16 and connected to the base 14 by positioning the sampling device 11 thereon without requiring manipulation of the coupler 16 itself. In another embodiment, the fluid sampling system 10 may be used without a coupler altogether, such that the sampling device 10 may be connected directly to the base 14. In such an embodiment, the sampling device 11 may include fasteners or latches which attach to the base 14, or may include clips which clip onto the base 14. In yet another embodiment, the sampling device 11 may include threads which mate directly onto threads located on the base 14. In another embodiment, the sampling device 11 and the base 14 may include magnets, such that the magnets may be used to connect the sampling device 11 to the base 14.

In the embodiment shown, the valves 20, 22, 28, 30 may be one-way valves, such as check-valves. In other embodiments, the valves 20, 22, 28, 30 may include different types of valves, for example butterfly valves. In one embodiment, the valves 20, 22, 28, 30 automatically close when the sampling device 11 is disconnected from the base 14. However, in other embodiments, the valves 20, 22, 28, 30 may be manual operation valves, or alternatively automatic valves with a manual operation override, such that they may be manually operated to be controlled as desired, i.e. open, closed or at a position therebetween.

Figure 4:
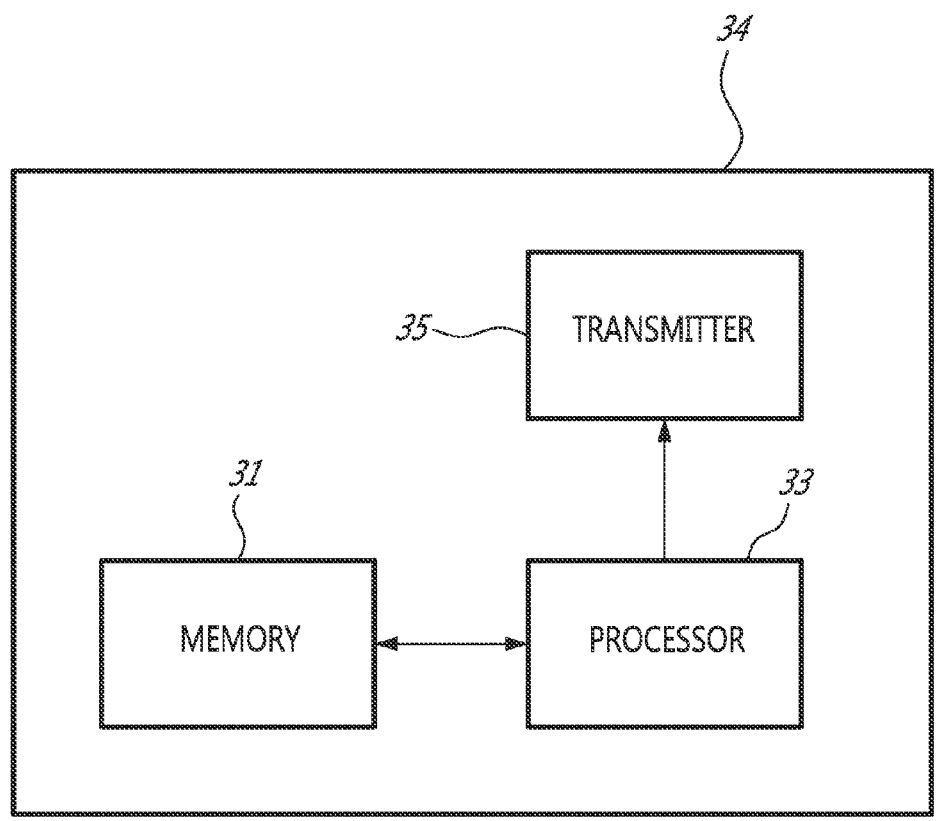
FIG. 4 is a block diagram of an exemplary embodiment for the data module.

In one embodiment, such as that illustrated in FIG. 2b, the recipient 12 may also comprise a data storage device 24, such as, for example, a random access memory (RAM). The data storage device 24 may be used to store information related to the fluid located inside the recipient 12. The information stored may include an identification number, the date, the time, the fluid flow or the fluid temperature of the fluid at the moment the fluid sample is collected, etc. In other embodiments, the information stored may comprise additional relevant data. The base 14 may also include a data module 34 which may be powered from a power source, such as an electrical connection, for example a battery, and which may be used to transmit information to the data storage device 24. In one embodiment, illustrated in FIG. 4, the data module 34 includes a memory 31 in which a unique identification number is permanently stored and means to record a current date and a current time, such as a processor 33. The data module 34 may also include sensors (not shown) for recording certain properties of fluid passing through the base 14, operation and environment parameters, or any additional relevant data. These properties may include fluid flow, fluid temperature, etc. A transmitter 35 sends the information from the data module 34 to the data storage device 24.

Figure 5:
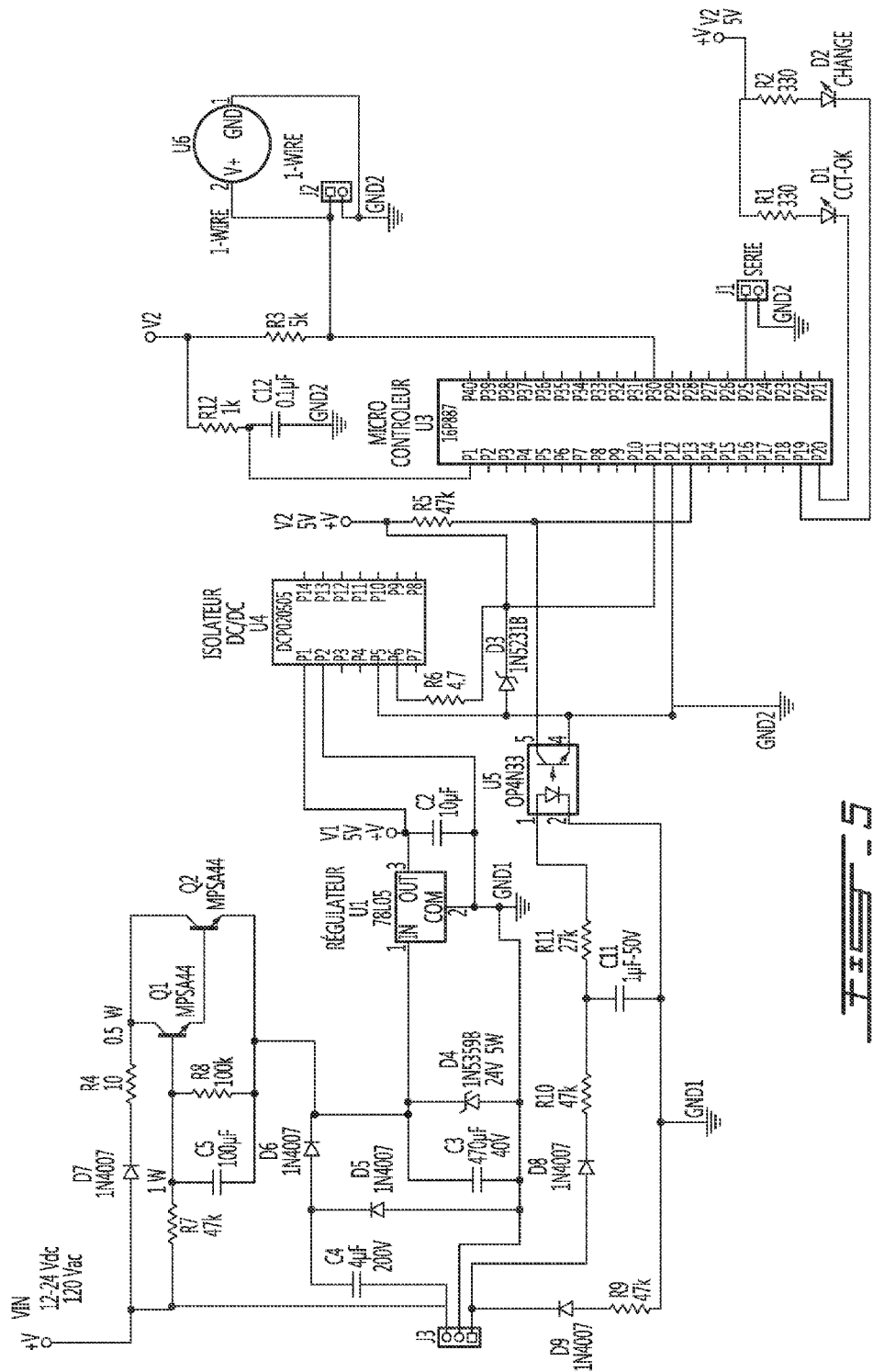
FIG. 5 is a circuit schematic of another exemplary embodiment for the data module.

In another embodiment, illustrated in FIG. 5, the data module 34 is an electrical circuit which stores the data and transmits it to the data storage device 24 upon connection. The circuit may comprise a micro-controller and other circuit elements such as transistors, resistors, capacitors, isolators, etc.

In one embodiment, the data module 34 need not be located on the base 14, but may be located directly on the machine. In yet another embodiment, the data module 34 need not be located on the machine, but may be located elsewhere, so long as the data module may be connected to the data storage device 24, and may transmit information, such as the identification number, thereto, and be associated with the machine.

When the base 14 is connected to the detachable sampling device 11, the data module 34 may be connected to the data storage device 24 of the recipient 12, through a direct contact or via wireless technology. When the data module 34 is connected to the data storage device 24 through a direct contact, the data module 34 may transmit data to the data storage device 24 through the contact, i.e. the data module 34 and the data storage device 24 form a closed circuit. When the data module 34 is connected to the data storage device 24 through wireless technology, the data module 34 may transmit data to the data storage device 24 through radio-frequency, infrared, microwaves, or other types of electromagnetic or acoustic waves. Any wireless technology used in cellular telephones, two-way radios, remote garage-door openers, television remote controls, and GPS receivers may be used. Various transmission protocols, such as WiFi, Bluetooth, and TCP/IP may be used.

The data module 34 may transmit the date, the time and the unique identification number to the data storage device 24 of the recipient 12. In one embodiment, the data module 34 may additionally transmit other relevant data, such as properties of the fluid sample, to the data storage device 24 of the recipient 12. The information transmitted to the data storage device 24 is then stored inside the data storage device 24.

Figure 6:
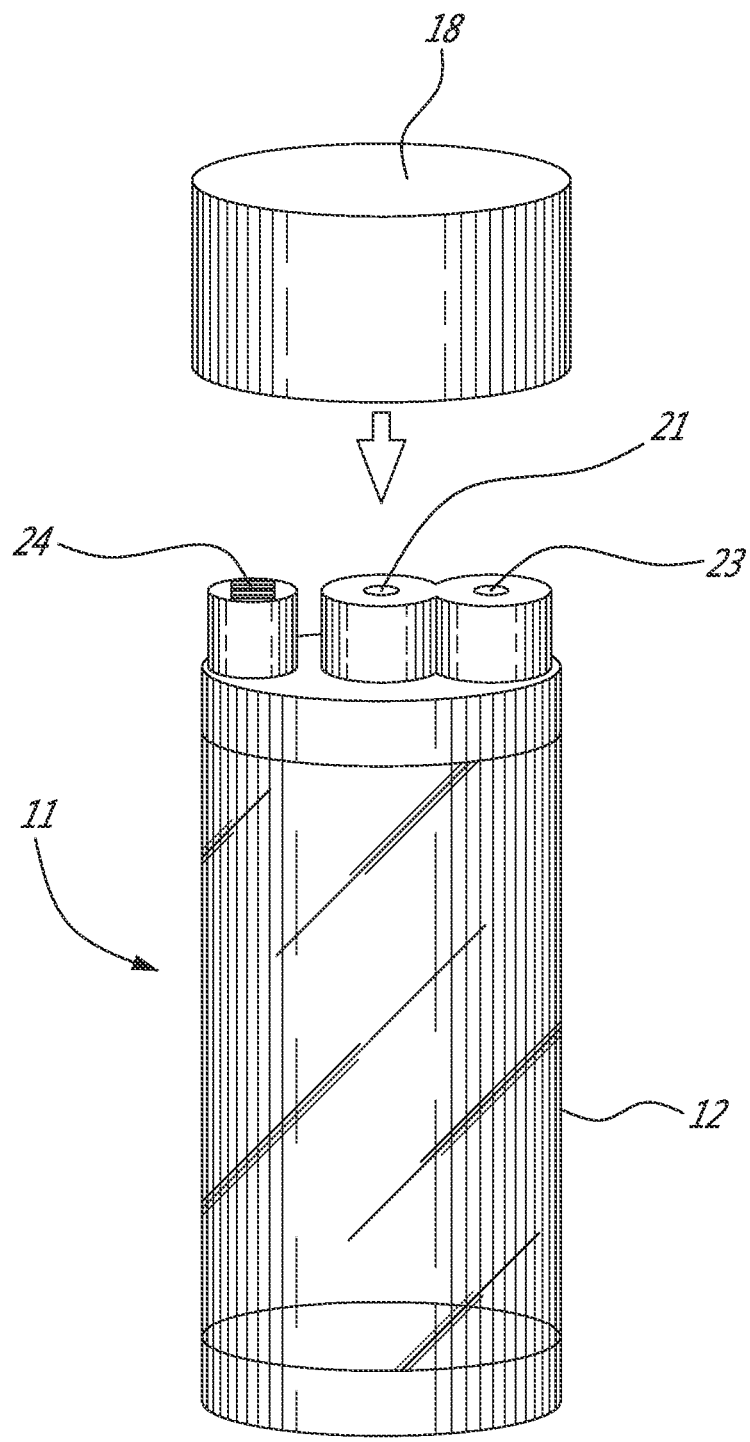
FIG. 6 is an exploded view of the sampling device of FIG. 3, in accordance with one embodiment.

FIG. 6 shows one embodiment of the sampling system 10, wherein the cap 18 has been removed from the bottom of the recipient 12 and is in the process of being placed on the top of the recipient.

Figure 7:
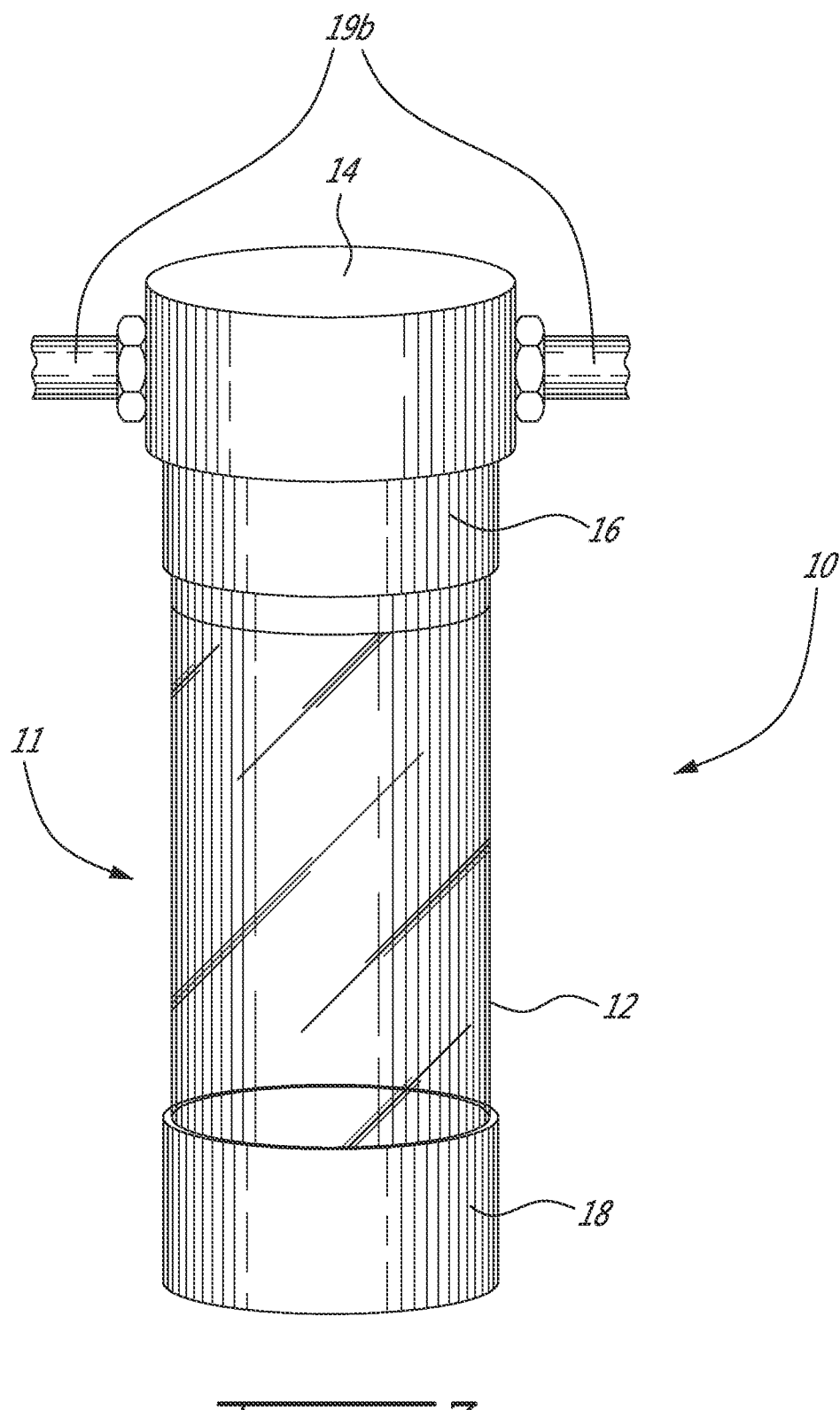
FIG. 7 is a perspective view, enlarged, of the fluid sampling system of FIG. 1, in accordance with one embodiment.

FIG. 7 shows an enlarged view of one embodiment of the sampling system 10, incorporated into the fluid system of a machine, with the coupler 16 in between the base 14 and the recipient 12, and the cap 18 attached to the bottom of the recipient 12.

In another embodiment of the sampling system 10, fluid flowing through the sampling system 10 may flow directly from the entrance conduit 26 to the exit conduit 30 and may only bifurcate into the sampling device 11, when a particular switch (not shown) is depressed.

In yet another embodiment of the sampling system 10, when the sampling device 11 is removed from the base 14, the fluid flowing through the sampling system 10 may be deviated such that it flows directly from the entrance conduit 26 to the exit conduit 30, i.e. fluid continuously flows through the system and it is simply deviated so as to bypass the sampling device 11 and be redirected through the base 14.

Figure 8:
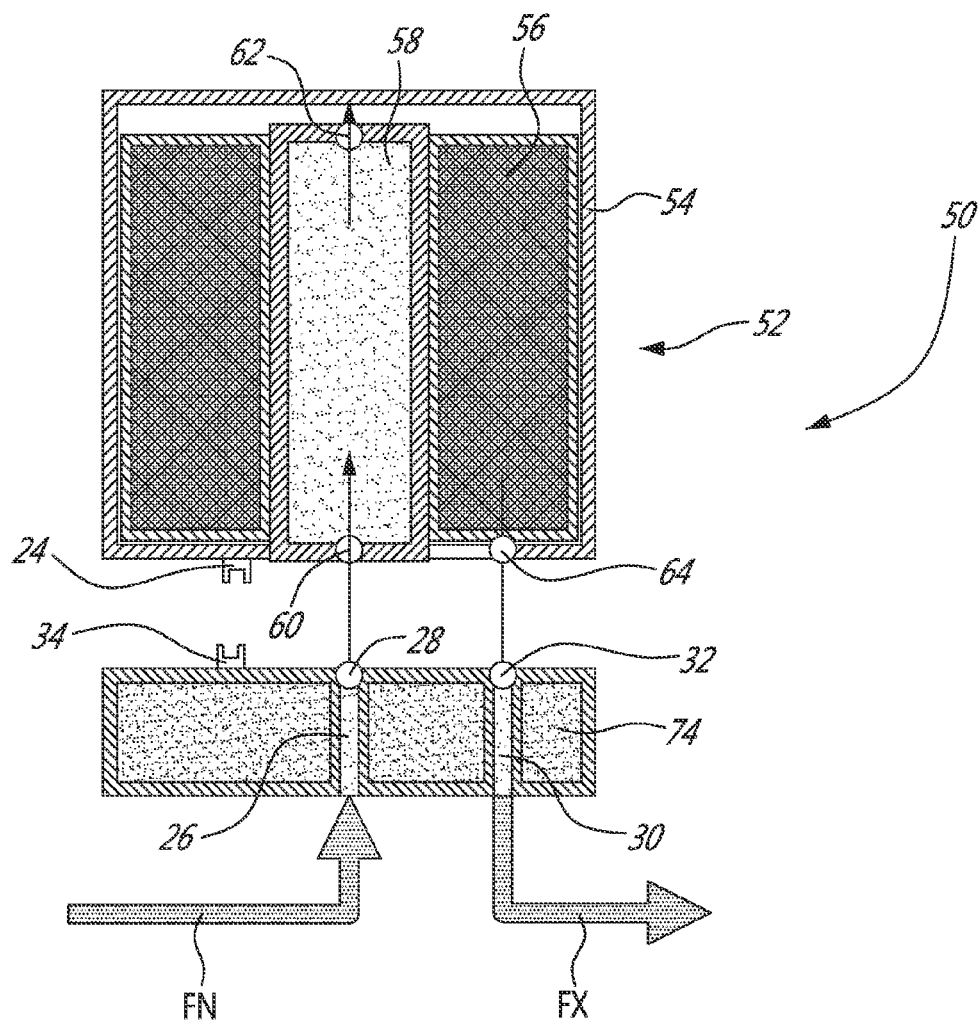
FIG. 8 is a schematic view of one embodiment of a sampling and filtration system, having a sampling recipient positioned inside a filter.

In another embodiment, as seen in FIGS. 8-11, a fluid sampling system is combined with a filtering system in order to obtain a detachable sampling and filtration system, for use in a fluid system of a machine. As seen in FIG. 8, a detachable sampling and filtration system 50 comprises a base 74 and a sampling and filtering device 52, which may be attached to the base 74. When the sampling and filtration system 50 is incorporated into a fluid system of a machine, fluid from the fluid system of the machine may enter the base 74 through fluid conduit FN, and may exit the base 74 through fluid conduit FX.

The sampling and filtering device 52 of FIG. 8 includes a housing 54 having both a filter 56, which may be annular, and a sampling recipient 58 which is circumscribed by said filter 56, located therein. In one embodiment, the sampling and filtering device 52 additionally includes the data storage device 24 and the base 74 includes the data module 34. The sampling and filtering device 52 may be attached to the base 74 using a number of different attachment means, such as fasteners, threads, latches, clips, etc. The sampling recipient 58 has an entry valve 60 and an exit valve 62, through which fluid may flow into and out of the recipient, respectively. The housing 54 includes an exit valve 64 through which fluid may flow out of the housing 54. When the sampling and filtering device 52 is attached to the base 74, the valves 28, 60, 62, 64, 32 may all be open, such that fluid may flow from the entrance conduit 26 into the sampling recipient 58, out of the sampling recipient 58 and into the housing 54, through the filter 56 inside the housing 54 and out of the housing 54 and into the exit conduit 30. In such a way, the fluid may pass into the sampling recipient 58 and subsequently be filtered before returning to the fluid system of the machine.

In one embodiment, when the sampling and filtering device 52 is connected to the base 74, the valves 28, 60, 62, 64, 32 automatically open to allow fluid passage therethrough, and when the sampling and filtering device 52 is disconnected from the base 74, the valves 28, 60, 62, 64, 32 automatically close to prevent fluid leakage therethrough. In another embodiment, the valves 28, 60, 62, 64, 32 may be manual operation valves, or alternatively automatic valves with a manual operation override, such that they may be manually operated to be controlled as desired, i.e. opened, closed or at a position therebetween.

When a fluid sample is to be collected, the sampling and filtering device 52 may be disconnected from the base 74. When the sampling and filtering device 52 is disconnected from the base 74, any fluid inside the sampling recipient 58 becomes enclosed therein. The data module 34 of the base 74 may transmit information to the data storage device 24. The sampling and filtering device 52 may then be sent to a laboratory for testing of the fluid sample, at which point, the information stored in the data storage device may be retrieved and used as desired.

Figure 9:
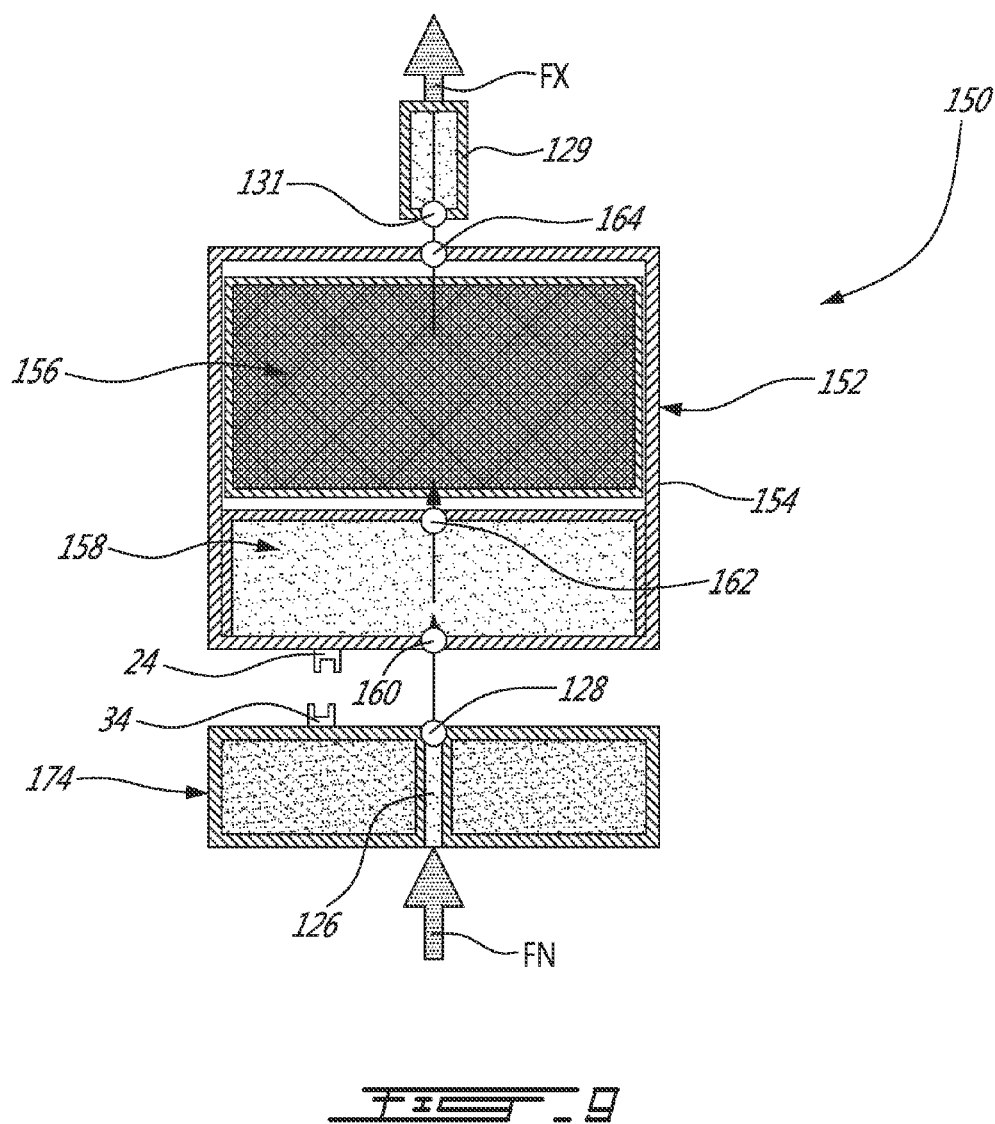
FIG. 9 is a schematic view of a second embodiment of the sampling and filtration system, having a sampling recipient and a filter which are sequentially positioned inside a housing.

In another embodiment, as seen in FIG. 9, a sampling and filtration system 150 may be positioned in serial flow communication with fluid conduits FN, FX of a fluid system of a machine. The sampling and filtration system 150 may comprise a disconnectable sampling and filtering device 152 which may be connected to a base 174. The base 174 includes an entrance conduit 126 with an exit valve 128 located therein, the entrance conduit 126 being in flow communication with a flow conduit FN of a fluid system of a machine. The sampling and filtering device 152 may include a housing 154 having both a sampling recipient 158 which is sequentially positioned with a filter 156, located therein. The sampling and filtering device 152 includes an entry valve 160 which controls fluid entry to the sampling recipient 158, an exit valve 162 which controls fluid leaving the sampling recipient 158 and entering the filter 156, and an exit valve 164 which controls fluid leaving the housing 154. A connection element 129 may also be provided with an entrance valve 131 therein, in order to connect the sampling and filtering device 152 to the flow conduit FX of the fluid system of the machine. In another embodiment, the sampling and filtering device 152 may be attached directly to fluid conduit FX, such that no connection element 129 is required.

As in the embodiment of FIG. 8, the sampling and filtering device 152 of FIG. 9 may be disconnected from the fluid system of the machine and sent to a laboratory for testing of the fluid sample inside the sampling recipient 158. The valves 128, 160, 162, 164, 131 may operate similarly to valves 28, 60, 62, 64, 32. In addition, before the sampling and filtering device 152 is disconnected from the base 174, the data module 34 may transmit information to the data storage device 24, the information being stored in the data storage device 24 for further use as desired.

Figure 10:
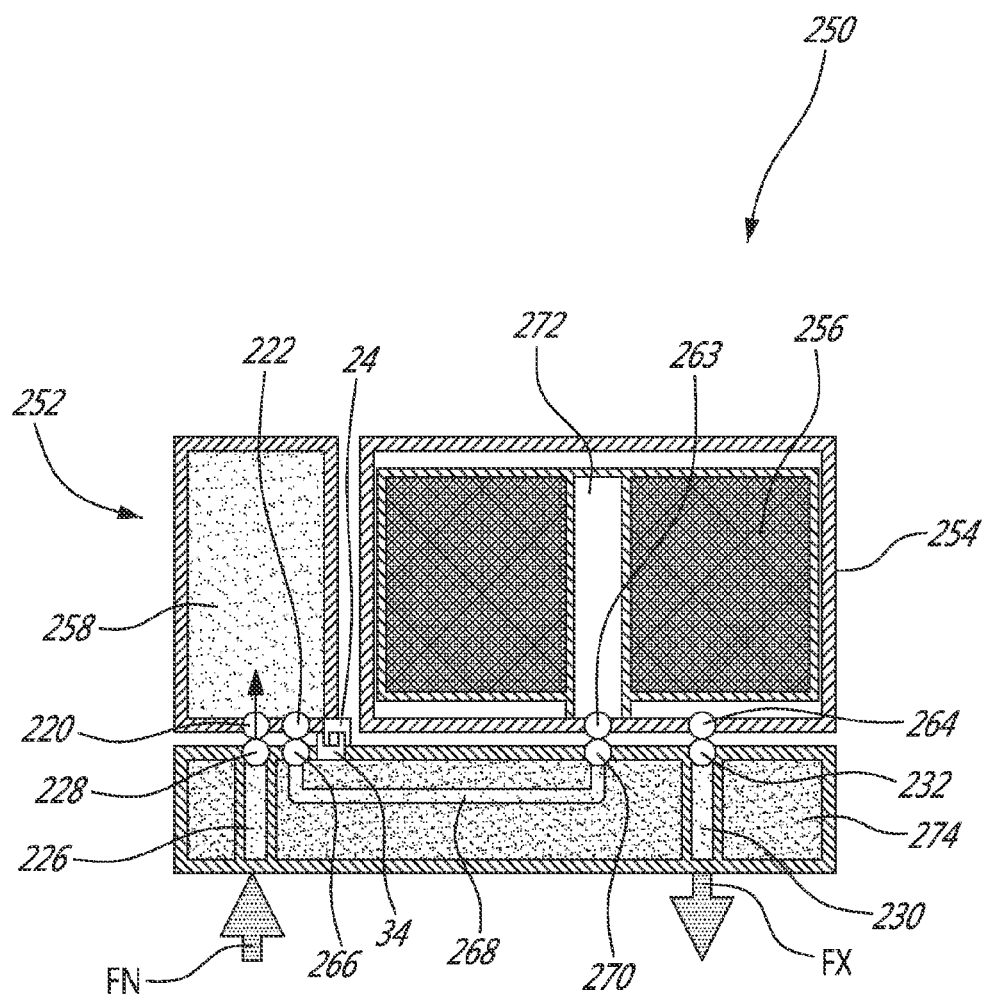
FIG. 10 is a schematic view of a third embodiment of the sampling and filtration system, having both a sampling recipient and a housing containing a filter, which are independent and which may both be separately attached to a common base.

In another embodiment, as seen in FIG. 10, the sampling and filtration system 250 may include a sampling and filtering device 252 in which the filter 256 and the sampling recipient 258 are independent of one another, i.e. are not both located inside the housing 254. As seen in FIG. 10, the sampling recipient 258 and the housing 254, in which the filter 256 is located, may be independently attached to a common base 274. In such an embodiment, the sampling recipient 258 may be removed from the sampling and filtration system 250 while leaving the housing 254 in which the filter 256 is located, attached thereon. Alternatively, both the sampling recipient 258 and the housing 254 in which the filter is located, may be removed as desired. As seen in FIG. 10, the base 274 includes an entrance conduit 226 which is in fluid flow communication with a fluid conduit FN of a fluid system of a machine, and an exit valve 228 located thereon. The sampling recipient 258 is attached to the base 274 and includes an entrance valve 220 which controls fluid entry into the sampling recipient 258, and an exit valve 222 which controls fluid exit from the sampling recipient 258. The base 274 also includes an entrance valve 266 which controls fluid entry from the sampling recipient 258 to the base conduit 268 of the base 274, and an exit valve 270 which controls fluid exit from the base conduit 268. The housing 254 includes an entrance valve 263 which controls fluid entry to a fluid passage 272 located inside the housing 254. Fluid passing through the fluid passage 272 then proceeds to flow through the filter 256 and afterwards may pass through the exit valve 264 which controls fluid exit from the housing 254. The base 274 further includes an entrance valve 232 which controls fluid entry to entrance conduit 230, which is in fluid flow communication with the fluid conduit FX of the fluid system of the machine.

In one embodiment, when the sampling recipient 258 is connected to the base 274, the valves 228, 220, 222, 266, 270, 263, 264, 232 may automatically open to allow fluid passage therethrough, and when the sampling recipient 258 is disconnected from the base 274, the valves 228, 220, 222, 266, 270, 263, 264, 232 may automatically close to prevent fluid leakage therethrough. In another embodiment, the valves 228, 220, 222, 266, 270, 263, 264, 232 may be manual operation valves, or alternatively automatic valves with a manual operation override, such that they may be manually operated to be controlled as desired, i.e. open, closed or at a position therebetween. In one embodiment, if the housing 254 is removed from the sampling and filtration system 250, the valves 270, 263, 264, 232 are closed. Similarly, if the sampling recipient 258 is removed from the sampling and filtration system 250, the valves 228, 220, 222, 266, are closed.

The sampling recipient 258 may be disconnected from the fluid system of the machine and sent to a laboratory for testing of the fluid sample located therein. In addition, before the sampling recipient 258 is disconnected from the base 274, the data module 34 may transmit information to the data storage device 24, the information being stored in the data storage device 24 for further use as desired. After the sampling recipient 258 has been removed, it may be replaced by a new sampling recipient which is attached to the base 274, which allows the sampling and filtration system 250 to continue filtering fluid passing therethrough.

Figure 11:
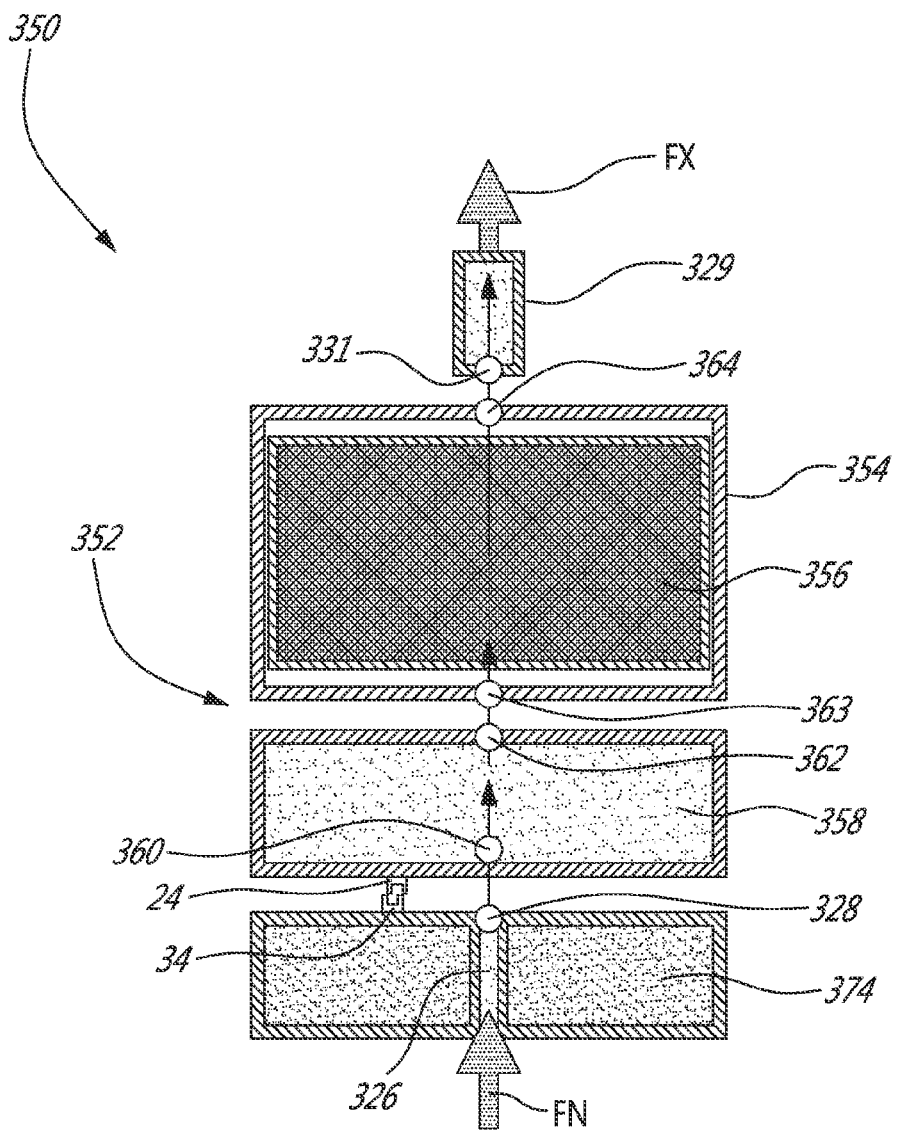
FIG. 11 is a schematic view of a fourth embodiment of the sampling and filtration system, having a sampling recipient and a housing containing a filter, which are independent and which are sequentially disposed.

In another embodiment, as seen in FIG. 11, the sampling and filtration system 350 is in serial flow communication with fluid conduits FN, FX of a fluid system of a machine. The sampling and filtration system 350 includes a base 374 which may be connected to the detachable sampling and filtering device 352. The detachable sampling and filtering device 352 includes a sampling recipient 358 and a housing 354 having a filter 356 located therein. The sampling recipient 358 may be connected to the housing 354, which may be connected to a connection element 329. The sampling and filtration system 350 differs from the sampling and filtration system 150 shown in FIG. 9, in that the sampling recipient 358 is not located inside the housing 354 with the filter 356. As seen in FIG. 11, the sampling recipient 358 is independent and separate from the filter 356 and the sampling recipient 358 and the housing 354, in which the filter 356 is located, are sequentially disposed.

Similarly to the embodiment shown in FIG. 10, the sampling recipient 358 may be removed from the sampling and filtration system 350 without removing the filter 356, or alternatively, the filter 356 may be removed along with the sampling recipient 358 if desired. The base 374 includes an entrance conduit 326 which is in fluid flow communication with a fluid conduit FN of a fluid system of a machine, and an exit valve 328 controls fluid flow out of entrance conduit 326. The sampling recipient 358 includes an entrance valve 360 which controls fluid flow into the sampling recipient 358 and an exit valve 362 which controls fluid flow out of the sampling recipient 358. The housing 354 includes a filter 356 through which fluid may flow, an entry valve 363 which controls fluid flow into the housing 354, and an exit valve 364 which controls fluid flow out of the housing 354. The connection element 329 may be connected to the housing 354 and is in fluid flow communication with the fluid conduit FX of the fluid system of the machine, and includes an entrance valve 331 which controls fluid entry into the connection element 329. In another embodiment, the housing 354 may be attached directly to fluid conduit FX, such that no connection element 329 is required.

In one embodiment, when the sampling recipient 358 is connected to the base 374 and when the housing 354 is connected to the sampling recipient 358, the valves 328, 360, 362, 363, 364, 331 are open to allow fluid passage through the sampling and filtration system 350, and when the sampling recipient 358 is disconnected from the base 374, the valves 328, 360, are closed to prevent fluid passage through the sampling and filtration system 350. When the housing 354 is disconnected from the sampling recipient 358, the valves 362 and 363 are closed to prevent fluid passage through the sampling and filtration system 350.

The sampling recipient 358 may be disconnected from the fluid system of the machine and sent to a laboratory for testing of the fluid sample located inside the sampling recipient 358. In addition, before the sampling recipient 358 is disconnected from the base 374, the data module 34 may transmit information to the data storage device 24, the information being stored in the data storage device 24 for further use as desired. After the sampling recipient 358 has been removed, it may be replaced by a new sampling recipient which is attached to the base 374, which allows the sampling and filtration system 350 to continue filtering fluid passing therethrough.

It should be understood that the sampling and filtration systems 50, 150, 250, 350 shown in FIGS. 8-11 should not be limited to the orientation in which they appear in the figures. In other embodiments, the sampling and filtration systems 50, 150, 250, 350 may be differently oriented.

Figure 12:
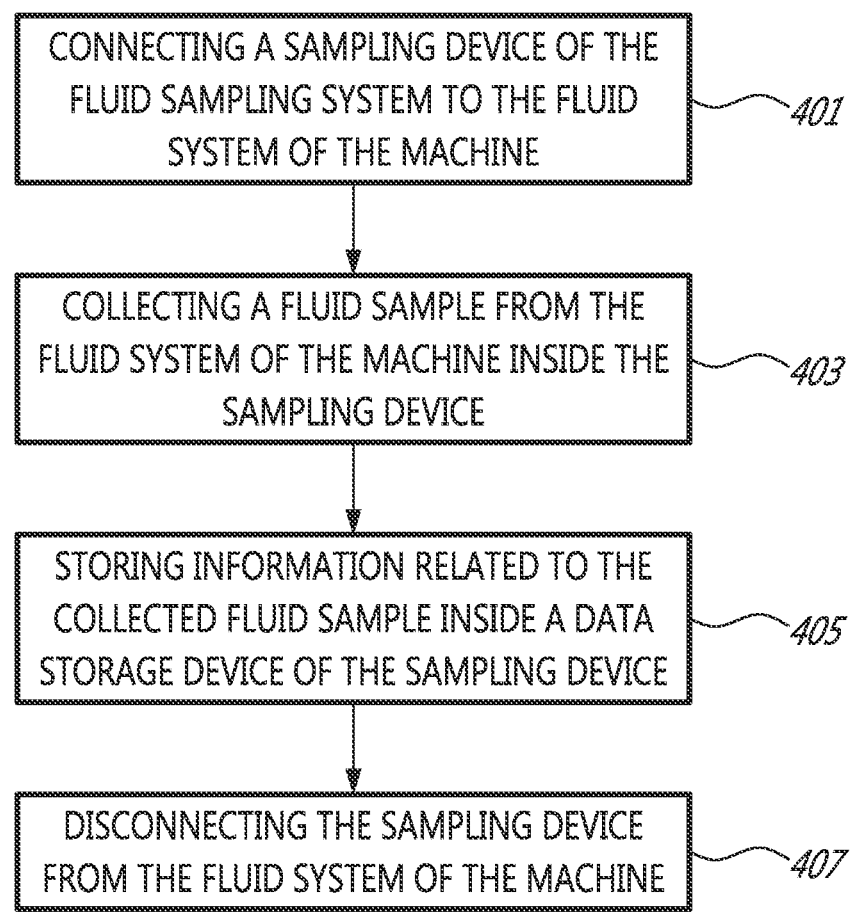
FIG. 12 is a flowchart of a method for collecting a fluid sample from a fluid system of a machine, in accordance with one embodiment.

The flowchart of FIG. 12 illustrates a method for collecting a fluid sample for a fluid system of a machine, in accordance with one embodiment. A sampling device is connected to a fluid system of a machine 401. The connection may be done using various means, such as those illustrated in FIGS. 1 to 11 and described above. Once connected, the fluid sample is collected from the fluid system of the machine inside the sampling device 403. Collecting can occur automatically, i.e. without any intervention from an operator, or it can be triggered by an operator using mechanical means provided on the sampling device, the base, the fluid system of the machine, or a combination thereof.

Before, after, or while the fluid sample is collected, information relating to the fluid sample and/or the machine from which the sample is being collected is stored with fluid 405. The information may be stored in a storage device integrated with the sampling device, as illustrated in FIG. 2b and described above, or in a storage device external to the sampling device but associated thereto. Once the fluid is collected, the sampling device is disconnected from the fluid system 407 and the sampled fluid and data are kept together.

During the period in which the sampling device is attached to the base, the data module and/or the data storage device may monitor properties of the fluid flowing through the sampling device and may store information related to the collected fluid sample as well as operation and environment parameters, or any additional relevant data, inside the data storage device. When desired, the user may disconnect the sampling device 11, which contains a fluid sample in the recipient 12 therein, from the base 14. Upon removal of the sampling device 11, the data module may transmit the date and/or time of removal and/or other relevant information, such as fluid properties before removal of the sampling device, to the data storage device 24. The user may then remove the cap 18 from the bottom of the recipient and may attach the cap 18 on the upper portion of the recipient 12. The user may then send the sampling device 11 to a fluid analysis facility.

For analysis purposes, the information stored on the data storage device 24 may be used in order to expedite the analysis of the fluid sample, i.e. provide a standardized method of identifying the fluid sample found in recipients 12, 58, 158, 258, 358, and may also be used to provide useful information for the analysis.

FIG. 13 illustrates a flowchart for a method of tracking a fluid sample collected from a fluid system of a machine, in accordance with one embodiment. A sampling device having the fluid sample contained therein is received 409. As described above, the sampling device has a data storage device with a unique machine identifier that corresponds to the machine from which the fluid was taken. The unique identifier associated with the machine is retrieved from the data storage device 411. Various fluid analysis tests are run on the fluid sample 13. Once the results of a fluid analysis are concluded, these results are then matched with the unique identifier 415.

The facility personnel receives the sampling device 11, removes the cap 18, extracts data stored inside the data storage device, such as the unique identifier, using a data extraction device, and proceeds to analyze the fluid sample using various instruments for analysis. The data extraction device may comprise a USB port such that a cable may be connected between the sampling device and a computer, a bar code reader, or various other data extraction means as known to a person skilled in the art. The extracted data is saved in a computer system, which may be connected to the computer server. The computer system may then associate the results of the fluid analysis of the collected fluid sample with the extracted data, including the unique identifier.

The extracted data and the fluid analysis results may be processed and organized into information which may be viewed, i.e. for example, in a database, a spreadsheet or a printout format. The data may be viewed locally, for example on a computer screen or on a printed sheet, or may alternatively be viewed remotely, such as via a website available to the public. In one embodiment, a user may access the computer server and consult, from a database, the information which corresponds to the fluid sample taken from the user's machine. In other embodiments, the sampling and filtration systems 50, 150, 250, 350 may be used in a similar application as that described for the sampling system 10.

The fluid system may include an oil lubrification system, a cooling/coolant or a heating system, a water distribution system, etc. In various embodiments, the fluid sampling system 10 or the sampling and filtration systems 50, 150, 250, 350 may be used in the oil lubrification system of, for example, industrial machines, such as heavy machinery, or in vehicles, such as trucks, tractors, cars, etc. In an oil lubrification system, the fluid sampling system 10 or the sampling and filtration systems 50, 150, 250, 350 may be used to collect oil samples. These oil samples may then be sent to a laboratory for analysis, in order to determine the quality of the oil and based on the results of an oil quality test, to determine whether the oil in the oil lubrification system should be changed. In an oil lubrification system, the sampling and filtration systems 50, 150, 250, 350 may be used not only to collect oil samples for further analysis, but also to serve as a filter for the oil, in order to ensure greater oil quality. The filter may thus serve to increase the useful life of the oil, which helps maintain the machine in greater condition, and reduces the number of times it is necessary to change the oil in the lubrification system.

As seen in the embodiment of FIG. 1, the sampling system 10 may be used in a secondary fluid conduit, such as a bypass fluid conduit. The sampling and filtration systems 50, 150, 250, 350 may also be used in a similar bypass conduit. In one embodiment the sampling and filtration system 50, 150, 250, 350 may be used in a bypass filtration system of, for example, an oil lubrification system. In this embodiment, the sampling and filtration systems 50, 150, 250, 350 may be used to complement a primary oil filtration system, while providing oil samples as needed.

In other embodiments, the sampling system 10 and the sampling and filtration systems 50, 150, 250, 350 may be used with other types of fluids such as, for example, water, air, coolants, cleaning liquids, etc. In one possible application involving water, the sampling system 10 and the sampling and filtration systems 50, 150, 250, 350 may be used in a water purification system.

The sampling system 10 and sampling and filtration systems 50, 150, 250, 350 therefore provide a number of uses. These systems ease the collection of fluid samples by limiting manipulations required from an operator. The systems allow for collection of a representative sample of fluid flowing in a fluid system. The systems help lower the risk of contaminating the fluid sample during the sampling procedure. The systems help minimize the risk of fluid leaking or spilling during the fluid sampling process. The systems create a standardized method of identification for the fluid sample, during the fluid sampling process and at the laboratory, and thereby minimize misidentification of the fluid sample. The systems allow for a regular monitoring of fluid circulating in a machine. In an oil lubrification system, the systems may help to reduce oil consumption through regular monitoring of the quality of the oil and helping to ensure that oil is only changed when necessary. This may increase the durability of the machine or equipment in which the oil circulates, by helping to ensure that only oil of acceptable quality circulates in the machine or equipment.

While the steps of the methods illustrated in FIGS. 12 and 13 are shown as occurring in a particular order, it will be appreciated by those skilled in the art that many of the steps are interchangeable and may occur in different orders than that shown without materially affecting the end results of the methods. Additionally, while the present disclosure relates to code or functions that reside in a data module, this is not meant to limit the scope of possible applications of the described methods and module. Any system that utilizes static code on any type of computer readable medium, could be utilized without causing departure from the spirit and scope of the present disclosure.

The example embodiments of the present disclosure described above are intended to be examples only. Those of skill in the art may effect alterations, modifications and variations to the particular example embodiments without departing from the intended scope of the present disclosure. In particular, selected features from one or more of the above-described example embodiments may be combined to create alternative example embodiments not explicitly described, features suitable for such combinations being readily apparent to persons skilled in the art. The subject matter described herein in the recited claims intends to cover and embrace all suitable changes in technology.

We claim:

1. A fluid sampling and filtering comprising:
   a bypass fluid conduit attachable to a primary fluid conduit of a fluid system of a machine;
   a base mounted to the bypass fluid conduit and having a base entrance conduit in fluid communication with the bypass fluid conduit for receiving fluid from the fluid system through the bypass fluid conduit, and a base exit conduit in fluid communication with the bypass fluid conduit for returning fluid back to the fluid system through the bypass fluid conduit;
   a sampling and filtering device detachably connectable to the base for fluid flow communication therewith; the device comprising:
   a housing defining an enclosure and having a housing exist valve in communicative flow with the base exit conduit to return fluid from the housing into the base;
   a sampling recipient in the housing for collecting a sample of the fluid, the sampling recipient having a recipient entry valve in communicative flow with the base entrance conduit to receive the sample of fluid from the base, and a recipient exit valve in communicative flow with the enclosure of the housing and through which the sample of fluid exists the sampling recipient and flows into the enclosure of the housing; and
   a filter in the housing that circumscribes the sampling recipient and is positioned in the enclosure to filter fluid that exists the sampling recipient exit valve before being expelled through the housing exit valve;
   wherein the recipient entry valve, the recipient exit valve, and the housing exit valve are configured to open when the sampling and filtering device is connected to the base and to close upon disconnection of the sampling and filtering device from the base;
   a data module on the base configured to store a unique machine identifier; and;
   a data storage device on the sampling and filtering device configured to receive the unique machine identifier from the data module when the sampling and filtering device is connected to the base.

2. The sample system of claims 1, further comprising a coupler which interconnects the sampling and filtering device to the base.

3. The system of claim 1, further comprising a cap attachable to the bottom end of the sampling and filtering device when the sampling and filtering device is connected to the base and attached to a top end of the sampling and filtering device when the sampling and filtering deice is disconnected from the base.

4. The system of claim 1, wherein the sampling and filtering device comprises at least one fastener to attach the sampling and filtering device to the base.

5. The sampling system of claim 1, wherein the data module stores additional information regarding the machine and the fluid system, and the data storage device is adapted to receive and store the additional information.

6. The system of claim 1, wherein the data storage device is further configured to store a date and a time at which the fluid sample is collected.

7. The system of claim 1, wherein the data module is further configured to store a date and a time and to transmit the date and time to the data storage device with the unique machine identifier.

8. The system of claim 1, wherein the data module is further configured to store properties of the fluid sample and to transmit the properties of the fluid sample to the data storage device with the unique machine identifier.

9. The system of claim 1, wherein the data module and the data storage device are further configured to communicate via wireless technology.

\* \* \* \* \*